US009638613B2

(12) United States Patent
Chapman

(10) Patent No.: US 9,638,613 B2
(45) Date of Patent: May 2, 2017

(54) HOSE KINK RESISTANCE TESTING DEVICE

(71) Applicant: TEKNOR APEX COMPANY, Pawtucket, RI (US)

(72) Inventor: Timothy L. Chapman, Stanton, TN (US)

(73) Assignee: TEKNOR APEX COMPANY, Pawtucket, RI (US)

(*) Notice: Subject to any disclaimer, the term of this patent is extended or adjusted under 35 U.S.C. 154(b) by 230 days.

(21) Appl. No.: 14/445,841

(22) Filed: Jul. 29, 2014

(65) Prior Publication Data

US 2016/0003723 A1 Jan. 7, 2016

Related U.S. Application Data

(60) Provisional application No. 62/021,373, filed on Jul. 7, 2014.

(51) Int. Cl.

| | |
|---|---|
| ***G01N 3/26*** | (2006.01) |
| ***G01F 1/00*** | (2006.01) |
| ***G01L 3/00*** | (2006.01) |
| ***G01N 3/12*** | (2006.01) |

(52) U.S. Cl.

CPC ................ *G01N 3/26* (2013.01); *G01F 1/00* (2013.01); *G01L 3/00* (2013.01); *G01N 3/12* (2013.01)

(58) Field of Classification Search

CPC ........................................ G01N 3/26

USPC ........................................ 73/37

See application file for complete search history.

(56) References Cited

U.S. PATENT DOCUMENTS 1,512,063 A 9/1921 Sproull
1,608,067 A 5/1925 Hull
5,339,677 A 8/1994 Haug
5,661,247 A * 8/1997 Hooke .................... G01N 3/22 73/800
6,321,596 B1 * 11/2001 Newman ................ E21B 19/22 73/152.45
8,554,497 B2 10/2013 Hamilton et al.
8,667,854 B2 * 3/2014 Nishioki ................ G01L 3/106 73/780

FOREIGN PATENT DOCUMENTS

CN 100541166 C 9/2009
JP 2005-24297 A 1/2005
JP 2005024297 A * 1/2005 .............. G01N 3/00
WO 2013136927 A1 9/2013

* cited by examiner

*Primary Examiner* — John Fitzgerald
*Assistant Examiner* — Jean Morello
(74) *Attorney, Agent, or Firm* — Hudak, Shunk & Farine Co. LPA

(57) ABSTRACT

A device and methods for testing and quantifying the kink resistance of a hose. The device has the ability to simultaneously test a plurality of hoses at equal amounts of twist or torque while water or other fluid is pumped through the hoses. The device can monitor one or more of the flow rate of fluid through a hose, fluid backpressure from a pressure source, torque and degrees of hose twist.

20 Claims, 5 Drawing Sheets

10
12
14
16
20
22
24
26
28
30
34
40
44
46
48
57
61
62
70
74
76
110
112

62
34
32
30
34
61
16
57
20

HOSE KINK RESISTANCE TESTING DEVICE

FIELD OF THE INVENTION

The present invention relates to a device and methods for testing and quantifying the kink resistance of a hose. The device has the ability to simultaneously test a plurality of hoses at equal amounts of twist or torque while water or other fluid is pumped through the hoses. The device can monitor one or more of the flow rate of fluid through a hose, fluid backpressure from a pressure source, torque and degrees of hose twist.

BACKGROUND OF THE INVENTION

It is desirable for hose manufacturers to test hoses, in particular garden hoses, utilizing the same or similar treatment as the hoses are likely to receive when in actual use. As such, various devices have been proposed in the art.

U.S. Pat. No. 1,512,063 relates to a device for testing short lengths of hose, and particularly hose which is subjected to a considerable fluid pressure or heat and pressure when in use, such as air-brake and steam hose for railway trains. One object is to provide a means for imparting bending movements to the test pieces, preferably while under fluid pressure, of a character more or less simulating the bending movements in actual service, but rapidly repeated so as to obtain an accelerated break-down test whereby the life of different constructions and qualities may be compared.

U.S. Pat. No. 1,608,067 relates to an apparatus by which a hose can be tested for any defects prior to being put in use. The apparatus aims to subject the hose during its testing operation to substantially the treatment as it is likely to get when in actual use, and thereby develop any weaknesses that will otherwise appear after the hose has gone in use.

Chinese Patent No. 100541166 C and Japanese Publication No. 2005-24297 relate to tubular body performance comparison display devices for comparing visually the performance of an elastically deformable tubular body such as a tube or a hose.

SUMMARY OF THE INVENTION

In view of the above, one problem of the present invention was to provide a device that quantifies the kink resistance of a hose.

Still another problem of the invention was to provide a device that allows side by side, visual comparison of two hoses simultaneously while a fluid is circulated through the hoses, and further to provide the ability to objectively measure one or more of hose twist, fluid flow rate, backpressure and torque.

The noted problems and others of the invention are overcome by the devices described herein which provide for testing of and quantification of the kink resistance of a hose.

One object of the present invention is to provide a device for twisting a hose in a circumferential direction while circulating fluid through the hose, wherein the device can also measure or monitor one or more of flow rate of the fluid through the hose, degrees of hose twist, backpressure from a pressure source and torque.

Another object of the present invention is to provide a device that allows side by side, visual comparison testing of two hoses simultaneously during fluid circulation.

Still another object of the present invention is to provide a device having a fluid reservoir including a fluid and a pressure source such as a pump that is capable of supplying fluid at a desired pressure and flow rate to one or more hoses that can be twisted or rotated in a circumferential direction while the fluid is passed through the hose(s).

A further object of the present invention is to provide a device that is capable of quantifying reduction in fluid, e.g. water, flow, that results from twisting a hose in a circumferential direction.

Yet another object of the present invention is to provide a device that has the ability to adjust fluid flow rate through two or more fluid circuits and thus two or more hoses, preferably such that the flow rate is equal or substantially equal between the hoses to be tested, and further has the ability to simultaneously twist each hose in a circumferential direction in order to quantify the kink resistance of a hose and measure or monitor at least one of the properties disclosed herein. Accordingly, in one aspect of the invention a hose testing device is disclosed, comprising a fixture for receiving a hose, the fixture having a first fitting operatively connectable to a first end of the hose and a second fitting operatively connectable to a second end of the hose, such that a liquid can be transferred from the first fitting, through the hose, and then out through the second fitting at least during a time when the hose is not subjected to twisting; a fluid reservoir including a liquid and a pressure source capable of supplying the liquid at a pressure to the hose through the first fitting; and a twist-inducing mechanism operatively connected to the hose through the first fitting such that the hose can be rotated in a circumferential direction while the second fitting does not rotate and the liquid flows through the hose.

In another aspect, a hose testing device is disclosed, comprising a first fluid circuit including a fluid reservoir including a fluid, a pressure source that is capable of transporting the fluid from the fluid reservoir through a first fitting, a hose, a second fitting, and then back to the fluid reservoir, wherein the hose is connected to the first fitting such that a gear system of the device is able to rotate the hose in a circumferential direction while the second fitting remains stationary and the pressure source transports the fluid through the hose.

In yet another aspect, a method for testing kink resistance of at least two hoses is disclosed, comprising the steps of connecting a first hose to a first inlet and a first outlet of a hose testing device; connecting a second hose to a second inlet and a second outlet of the hose testing device; flowing a fluid through the first inlet, through the first hose and out through the first outlet and through the second inlet, through the second hose and out through the second outlet; and twisting the first hose and the second hose in a circumferential direction simultaneously at a same degree of twist while the fluid flows through the first hose and the second hose.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

The hose kink resistance testing device provides visual feedback as well as informative data regarding the flow rate of a fluid through the hose, preferably water in one embodiment, as well as degrees of hose twist, pressure source backpressure, and information regarding torque. When two or more hoses are tested simultaneously, an observer can visually assess the kink resistance thereof in addition to being able to monitor and/or record other data produced during testing. Advantageously, the testing device of the present invention can be utilized to simulate relatively normal testing conditions that a hose would be subjected to, as well as non-typical or extreme testing conditions.

Figure 1:
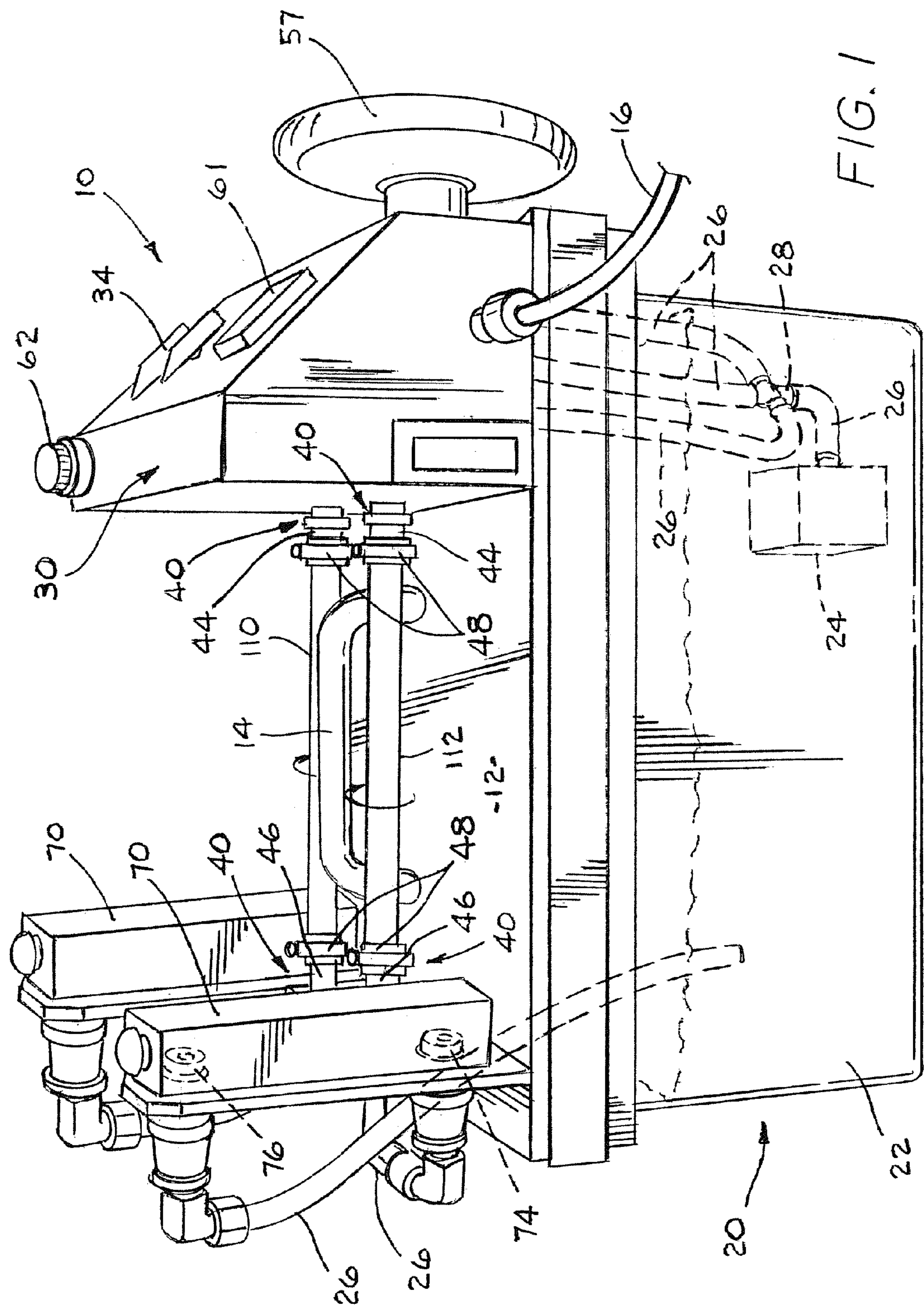
FIG. 1 is a downward looking side elevational view of one embodiment of a testing device of the present invention.

Referring now to the drawings wherein like reference numbers refer to like parts throughout the several views, a hose testing device 10 is illustrated therein. FIG. 1 illustrates base 20 of the device 10 that includes a fluid reservoir 22 that is adapted to hold a fluid that can be circulated through a hose such as first hose 110 or second hose 112 during the testing procedure. The fluid is preferably water or a fluid of similar viscosity. Other fluids may be used as appropriate for the product being tested. The fluid reservoir 22 can be formed from any desired material that is compatible with the fluid utilized. Suitable materials include, but are not limited to, various polymers or metals. The fluid reservoir 22 illustrated in FIG. 1 is a polymeric basin, more specifically polyethylene. The dimensions of the fluid reservoir 22 should be sufficient in order to hold a desired quantity of fluid. Although water is a preferred fluid, other liquids can also be utilized and the invention is not limited to any particular fluid. The temperature of the fluid can be varied in various embodiments. Heated or cooled fluid can be utilized to assess hose performance at non-typical conditions. A pressure source 24 is operatively connected to the fluid reservoir 22 that is capable of supplying the fluid at a desired pressure to a hose as described further herein. The pressure source 24 is a pump in a preferred embodiment. A suitable pump has a sufficient pressure to supply the fluid at a desired flow rate. For example, in one embodiment a submersible pump is utilized for testing garden hoses that has a maximum flow rate of 12.4 gallons per minute at 5 FT head at a maximum pressure of 10.6 psi developed. It is to be understood that other pumps can be utilized having different flow rates and backpressure in order to suitably test or compare different products, e.g., hydraulic hoses.

Figure 3:
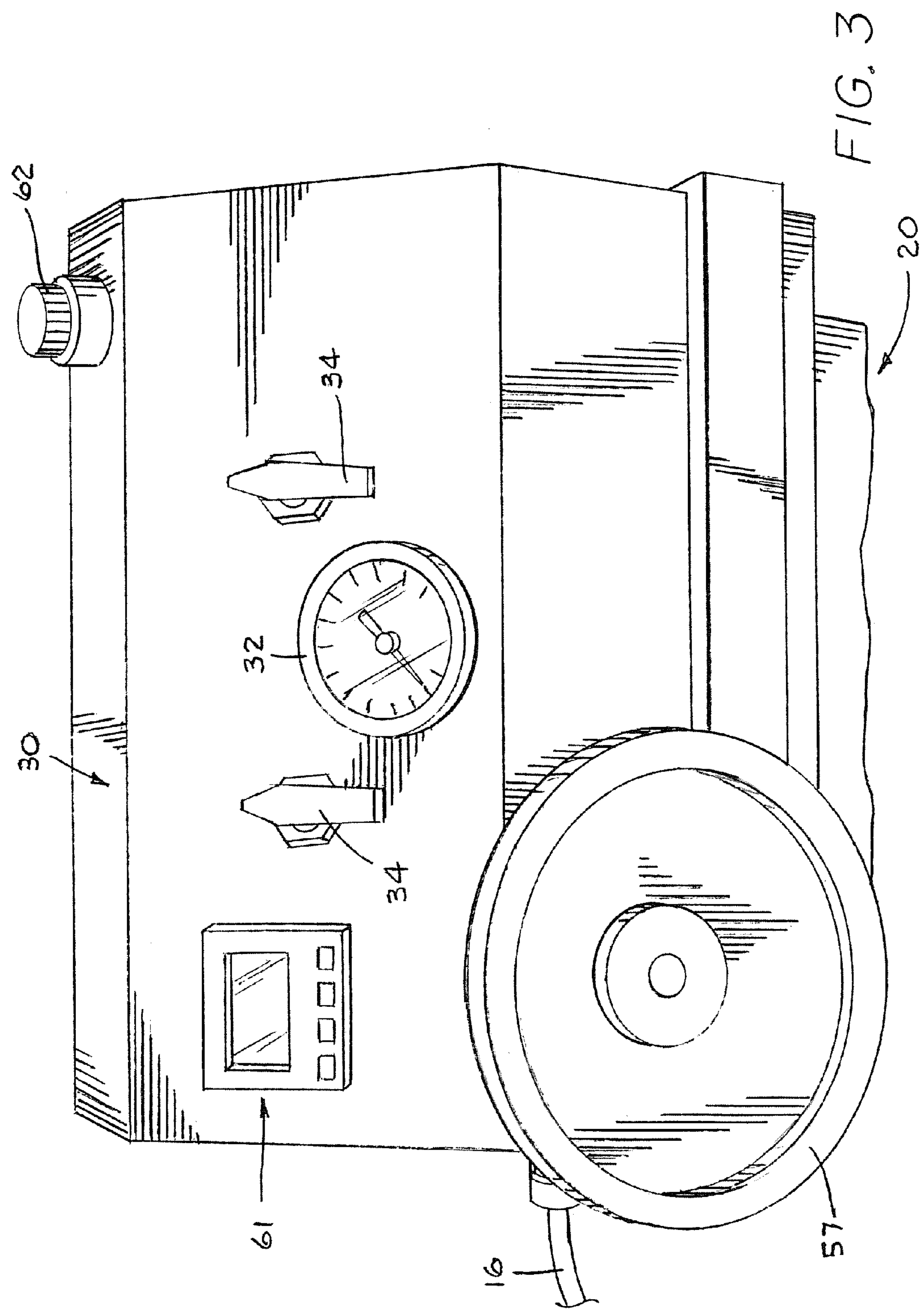
FIG. 3 is a front view of one embodiment of the testing device particularly illustrating a control panel.
Figure 5:
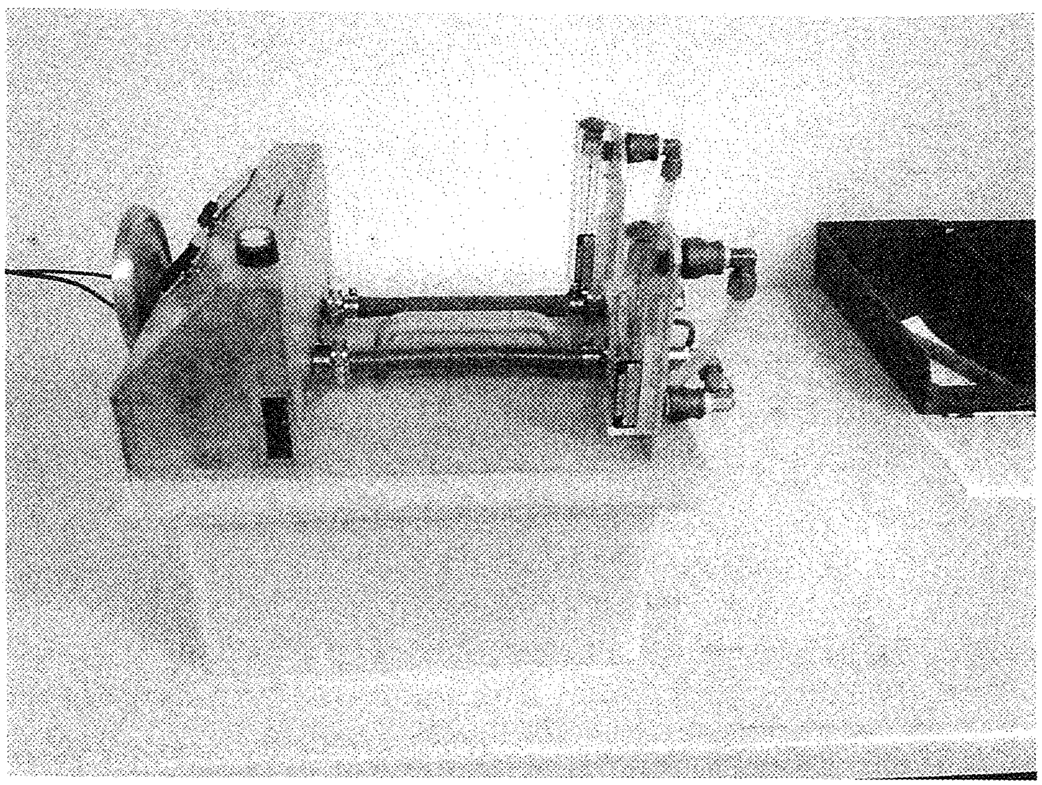
FIG. 5 is a downward looking side elevational photograph of one embodiment of a device of the present invention particularly illustrating a pair of hoses, each operatively connected to a separate testing fixture, with the hoses shown in an untwisted state not yet having undergone rotation in a circumferential direction.
Figure 6:
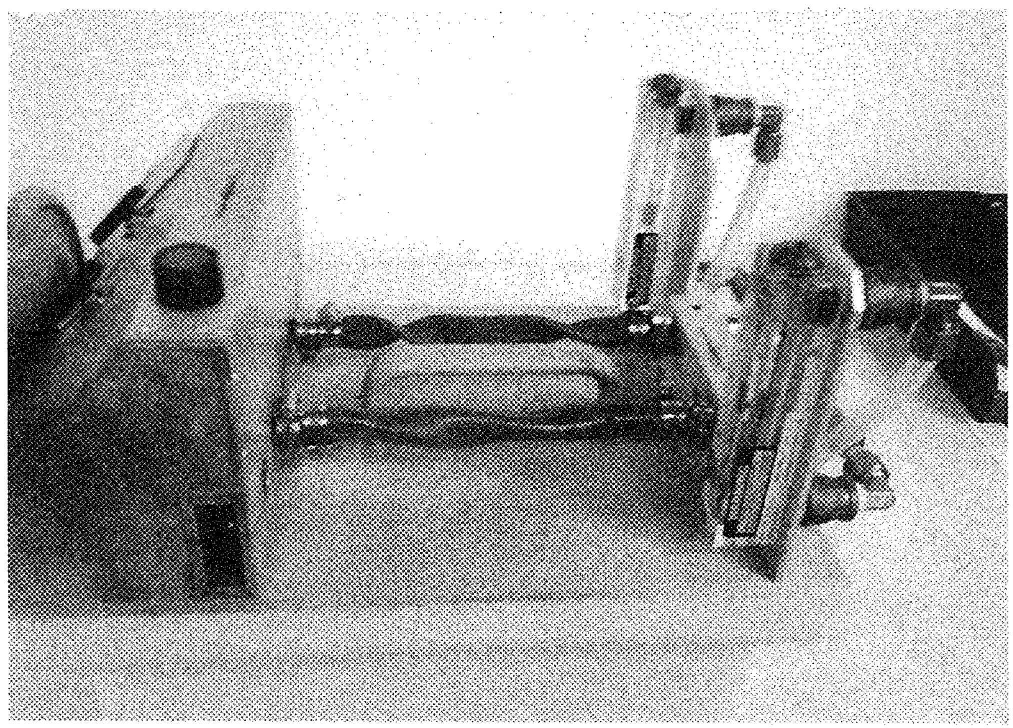
FIG. 6 illustrates a downward looking side elevational photograph of one embodiment of a device of the present invention particularly illustrating a pair of hoses, each operatively connected to a separate testing fixture, wherein the hoses have been twisted at one end in a circumferential direction so that a visual comparison of any kinking induced by the rotation can be visually assessed.

One or more fluid lines 26 are connected to and transfer fluid from the pressure source 24, preferably a pump, towards the one or more hoses present. In some embodiments, a fitting 28 is utilized to split a single fluid line 26 exiting the pressure source 24 into two or more fluid lines. Alternatively, multiple pumps could be used to provide an independent source of pressure and flow for each sample tested. That said, each hose to be tested may have an independent fluid circuit or share portions of one or more fluid lines with a fluid circuit of a second hose. Various tees are utilized to split the flow of one fluid line into two fluid lines, whereas a cross fitting 28 is utilized and illustrated in FIG. 1 to split the single fluid line from the pressure source 24 into three separate fluid lines 26. In the embodiment illustrated in FIG. 1, one of the fluid lines 26 downstream from fitting 28 is connected to a pressure gauge 32 mounted to control panel 30 as illustrated in FIG. 3. Pressure gauge 32 displays the backpressure of the pressure source 24. Pressure gauge 32 is chosen such that the maximum backpressure of the pressure source 24 is below the maximum display value of the pressure gauge. In one embodiment, the pressure gauge measures pressure up to 15 psi. In other embodiments, pressure sources providing relatively high flow and/or pressure are utilized. In a further embodiment, an electronic pressure transducer is installed in-line in one or more fluid circuits. Pressure, degrees of rotation and flow rate can be recorded and the data analyzed to predict hose performance under different situations.

The remaining fluid lines 26 downstream of fitting 28 are each routed through a separate valve 34, a ball valve in one embodiment, which are each utilized to regulate flow through each hose testing fixture 40. Each testing fixture 40 has a dedicated fluid circuit. After passing through the ball valve 34, the fluid line 26 is connected to a rotary union 42 of testing fixture 40, with the rotary union 42 including a first fitting 44 adapted to be operatively connected to a first end of the hose to be tested. Use of the rotary union 42 allows the hose first end to be connected to fitting 44 and twisted, with the device components upstream of the rotary union 42 in the fluid circuit remaining stationary.

Figure 2:
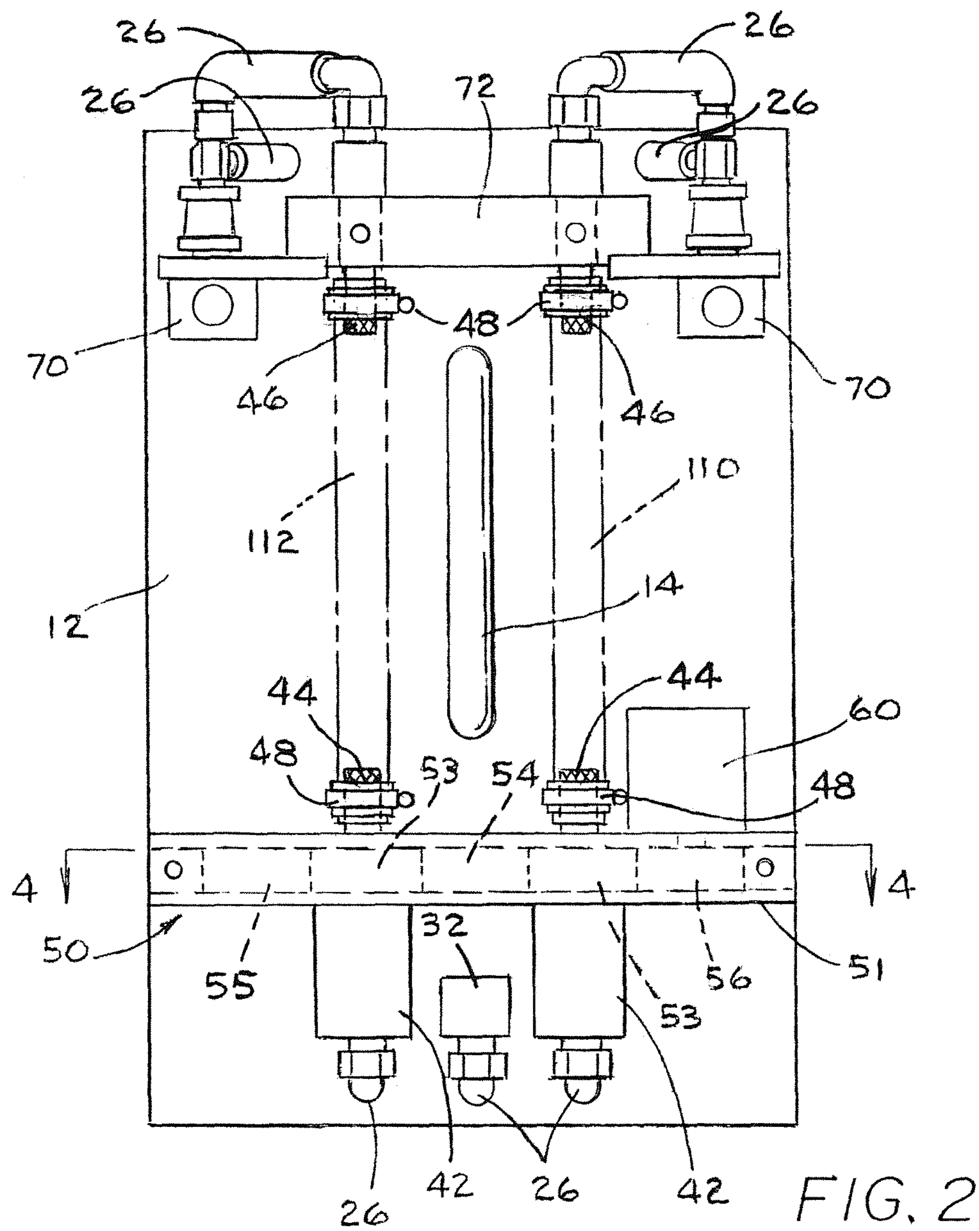
FIG. 2 is a top view of one embodiment of the testing device without the control panel.
Figure 4:
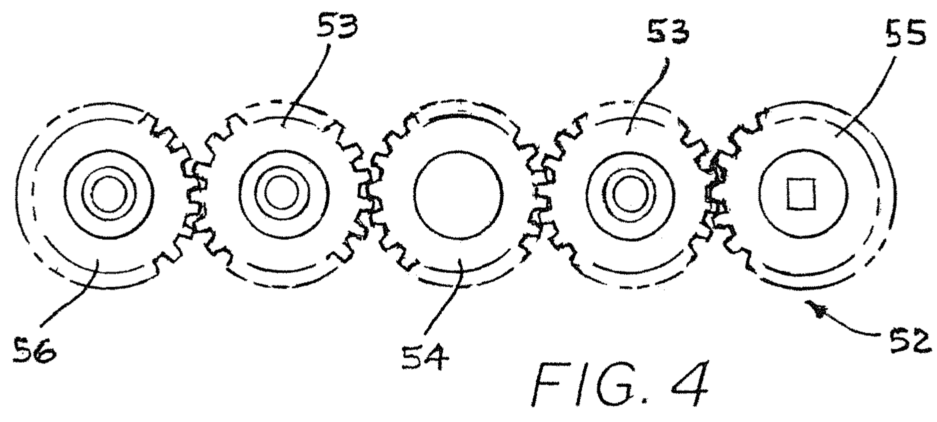
FIG. 4 illustrates one embodiment of a gear train of a gear system of the present invention that is utilized to impart the same twist to a pair of hoses, as viewed from the back of the device, opposite the front view including the control panel.

A gear system 50 is operatively connected to any rotary unions 42 present in the device in order to impart twist to the hose(s) present. The gear system 50 generally includes a housing 51, see FIG. 2, located within control panel 30, in which a gear train 52 is located, see FIG. 4, for example. The gear train 52 illustrated in FIG. 4 includes five (5) gears including a main drive gear 55 that is utilized to drive, directly or indirectly as desired, the remaining gears present in gear train 52. In the arrangement illustrated in FIG. 4, main drive gear 55 directly contacts and drives a hose drive gear 53, which in turn is operatively connected to idle gear 54. A second hose drive gear 53 is operatively connected to idle gear 54 on the opposite side of first hose drive gear 53. The purpose of the idle gears is to provide additional spacing between the hose test samples and to make both test samples rotate in the same direction. An encoder drive gear 56 is also operatively connected to hose drive gear 53 with the encoder utilized to measure the degrees of rotation of the hose or tube being tested. The encoder 60 includes an encoder display 61 located on the front of control panel 30 as illustrated in FIG. 3. The encoder is available from Dynapar. The encoder has a shaft with a flat section milled on it. This shaft is inserted into a hole in the encoder gear and secured with a set screw that rests against the flat section on the encoder shaft. Other arrangements can be used to connect the encoder of the device, if desired. Two inch pitch diameter gears are utilized in one embodiment, although different gearing may be utilized as known to those of ordinary skill in the art. Different size gears may be used in the same gear train to allow for different gear ratios between the drive and driven gears.

Rotation or twisting of the hose in a circumferential direction is accomplished in one embodiment through hand wheel 57, that as illustrated in FIGS. 1 and 3, is connected to drive gear 55, such as through a suitable square drive, for example, a ¼ inch or ⅜ inch square drive in various embodiments. Rotation of hand wheel 57 causes rotation of drive gear 55 which in turn drives the remaining gears 53, 54, 56 present. The rotary union 42 has male pipe threads (NPT, National Pipe Taper in one embodiment) that screw into mating female threads machined into hose drive gear 53. The rotary unions 42 may be sized to match the flow requirements of the product being tested. The first fitting 44 includes smooth and knurled sections. The smooth section forms a water tight seal between the hose and fitting 44. The knurled section contains raised metal such as arranged in a diamond pattern that provides a high friction surface that grips the hose material to prevent it from slipping on the fitting 44 when torque is applied A clamp or other securing element 40 can be used to additionally secure the sample or hose to the fitting.

Device 10 generally includes a fixture 40 as illustrated in the Figures, see especially FIG. 1, wherein two fixtures are illustrated, each adapted to receive a hose and having a first fitting 44 operatively connected to a first end of the hose, i.e., the inlet end, and a second fitting 46 operatively connectable to a second end of the hose, i.e., the outlet end, such that the fluid can be transferred from the first fitting 44 through the hose, and out through the second fitting 46. Due to the operative connection of the first fitting 44 to the gear system 50 of the invention, the first fitting 44, and thus the hose end connected thereto, can be rotated in a circumferential direction when the gear system 50 is actuated, such as through hand wheel 57. Second fitting 46 connected to the second or outlet end of the hose is a stationary fitting, thus rotation of the first fitting 44 causes any hose connected between first fitting 44 and second fitting 46 to be twisted. Second fitting 46 in one embodiment is also formed in a manner similar or identical to first fitting 44. Thus, the second fitting includes an outer, knurled section, see FIG. 2 for example, that serves as a high friction surface to connect the hose to the fitting and prevent it from slipping when torque is applied. Fitting 46 also includes a smooth section that forms a water tight seal between the hose and fitting 46. The smooth sections of the fittings are in contact with the outermost section of each end of the test sample or hose to prevent leakage.

Downstream from second fitting 46 a flow meter 70 is operatively connected to device 10 that displays the flow rate from the outlet of the hose to which the flow meter is operatively connected. In the embodiment in FIG. 1, second fitting 46 is connected to mounting bracket 72 along with flow meter 70. A fluid line 26 generally extends from the outlet of fitting 46 to the inlet 74 of flow meter 70. Any fluid entering flow meter 70 through inlet 74 proceeds through flow meter outlet 76 with the flow rate being displayed on flow meter 70. A suitable flow meter 70 is utilized that has the ability to display a desired flow range. In one embodiment, suitable to test garden-type hoses the flow meter has a flow rate range of 0.5 to 5 gallons per minute. Higher capacity gauges may be useful for other types of products and/or if a larger pump is utilized. Water exiting outlet 76 of flow meter 70 is returned to fluid reservoir 22 through an additional fluid line 26, see FIG. 1 for example.

As illustrated in FIG. 1, device 10 includes upper platform 12, upon which control panel 30 and mounting bracket 72 are located. The upper platform 12 also serves as a cover for fluid reservoir 22. A handle 14 can be present on device 10 in order to separate the upper platform from the base 20 for inspection, filling, or the like. A suitable power source 16 is utilized to provide a source of electrical energy for any of the components of the device that require the same. The power source 16 is utilized to power the pressure source 24, encoder 60 and torque analyzer 80.

The torque analyzer 80 in one embodiment is designed to be driven by a conventional ratchet wrench. A torque sensor 82 is installed between the ratchet and drive gear 55. The amount of torque required to deflect one sample is displayed on the hand-held display that is connected to the torque sensor. The torque analyzer 80 is most useful when testing single samples. During testing, the peak force required to take one sample or hose to 50% of original flow, or a "no flow" condition or any other condition can be recorded. The torque sensor 82 may not be used all of the time. It can be easily installed and removed from the device with no special tools as desired.

As illustrated in the various Figures, device 10 includes two different testing fixtures 40 that allow simultaneous testing of two hoses. It is to be understood that any number of additional testing fixtures can be added to the device or only one hose tested at a time by virtue of closing or shutting-off one of the valves 34 on control panel 30.

The device 10 of the present invention can be utilized in various embodiments as follows. A first hose, for example hose 110, is connected at a first end to first fitting 44 and at a second, outlet end to second fitting 46. Second hose 112 is connected between a separate fitting 44 and fitting 46. At this point in the process, the hoses 110 and 112 are connected such that the hoses are straight and un-twisted with respect to a circumferential or axial direction. A fluid is then circulated through the hoses by pressure source 24. Valves 34 are adjusted, if necessary, to equalize the flow rate through the hoses, when two or more hoses are to be tested simultaneously. Flow meter 70 displays the flow rate of the fluid through each particular hose. For example, in one embodiment a flow rate of about three gallons per minute is a general starting point for testing a garden hose. After a desired flow rate has been established, the hoses are twisted utilizing hand wheel 57 in an attempt to induce kinking and/or simulate use of the hose in an actual condition. The encoder 60 measures degrees of rotation from the starting point and displays the result on the encoder display 61. Button 62 located on the top right side of the control panel is a reset button that zeroes out the display 61 on the control panel 30 before the start of each test. The hand wheel 57 can be actuated until a desired degree of rotation or twist in a circumferential direction of the hose has been imparted thereto. During the twisting process, visual observations can be made comparing the deformation of each hose. Additionally, a separate flow meter 70 quantitatively measures the flow rate through the outlet of each hose. The torque analyzer displays the amount of torque required to deflect the one or more hoses being tested.

In view of the above description, a device and methods for testing and quantifying the kink resistance of a hose have been disclosed. The device allows for side by side visual comparison and observation of two or more hoses simultaneously. The device also provides quantitative results and flow rate changes for one hose or two or more hoses simultaneously can be quantified and recorded. Torque and backpressure measurements are also provided and are especially useful when performing detailed evaluation of a single sample or hose.

While in accordance with the patent statutes the best mode and preferred embodiment have been set forth, the scope of the invention is not limited thereto, but rather by the scope of the attached claims.

What is claimed is:

1. A hose testing device, comprising:

a fixture for receiving a hose, the fixture having i) a first fitting operatively connectable to a first end of the hose and rotatable in a circumferential direction of the hose and ii) a second fitting operatively connectable to a second end of the hose, such that a liquid can be transferred from the first fitting, through the hose, and then out through the second fitting at least during a time when the hose is not subjected to twisting;

a fluid reservoir including a liquid, and a pressure source capable of supplying the liquid at a pressure to the hose through the first fitting; and a twist-inducing mechanism operatively connected to the hose through the first fitting such that the hose can be rotated in a circumferential direction by the first fitting while the second fitting does not rotate and the liquid flows through the hose.

2. The hose testing device according to claim 1, wherein a flow meter is located downstream from the second fitting, and wherein the flow meter measures a flow rate of the liquid that is received from the second fitting.

3. The hose testing device according to claim 1, wherein an encoder is operatively connected to the twist-inducing mechanism and measures a degree of twist of the first fitting.

4. The hose testing device according to claim 1, wherein a torque analyzer is operatively connected to the twist-inducing mechanism and is able to quantify the amount of torque applied to the twist-inducing mechanism.

5. The hose testing device according to claim 1, wherein a pressure gauge is connected downstream from the pressure source and measures the pressure of the liquid received from the pressure source.

6. The hose testing device according to claim 1, wherein the twist-inducing mechanism includes a gear system having a drive gear one or more of directly and indirectly connected to a hose drive gear that operatively rotates the hose in the circumferential direction.

7. The hose testing device according to claim 6, wherein a second fixture for receiving a second hose is present and includes a first fitting operatively connectable to a first end of the second hose and a second fitting operatively connectable to a second end of the second hose such that the liquid can be transferred from the second fixture first fitting, through the second hose, and then out through the second fixture second fitting at least during a time when the hose is not subjected to twisting.

8. The hose testing device according to claim 7, wherein the gear system is constructed so that the first fixture first fitting and the second fixture first fitting rotate at the same rate.

9. A hose testing device, comprising:

a first fluid circuit including a fluid reservoir including a fluid, a pressure source that is capable of transporting the fluid from the fluid reservoir through a first fitting, a hose, a second fitting, and then back to the fluid reservoir, wherein the hose is connected to the first fitting such that a gear system of the device is able to rotate the hose in a circumferential direction while the second fitting remains stationary and the pressure source transports the fluid through the hose.

10. The hose testing device according to claim 9, wherein a flow meter is located in the fluid circuit downstream from the second fitting, and wherein the flow meter measures a flow rate of the liquid that is received from the second fitting.

11. The hose testing device according to claim 9, wherein an encoder is operatively connected to the gear system of the device and measures a degree of twist of the first fitting.

12. The hose testing device according to claim 9, wherein a torque analyzer is operatively connected to the gear system of the device and quantifies the amount of torque applied to the hose.

13. The hose testing device according to claim 9, wherein a pressure gauge is located in the fluid circuit downstream from the pressure source, wherein the pressure gauge measures a pressure of the fluid received from the pressure source.

14. The hose testing device according to claim 9, wherein the gear system has a drive gear one or more of directly and indirectly connected to a hose drive gear that operatively rotates the hose in a circumferential direction.

15. The hose testing device according to claim 9, wherein the device includes a fixture for receive a second hose, wherein the fixture includes a first fitting operatively connectable to a first end of the second hose and a second fitting operatively connectable to the second end of the second hose such that the fluid can be transferred from the fixture first fitting, through the second hose, and then out through the fixture second fitting whereby a second fluid circuit is present whereby the fluid can flow from the fluid reservoir through the fixture first fitting, the second hose, the fixture second fitting and then back to the fluid reservoir.

16. A method for circumferentially twisting at least two hoses, comprising the steps of:

connecting a first hose to a first inlet and a first outlet of a hose testing device;

connecting a second hose to a second inlet and a second outlet of the hose testing device;

flowing a fluid through i) the first inlet, through the first hose and out through the first outlet and through ii) the second inlet, through the second hose and out through the second outlet; and twisting the first hose and the second hose in a circumferential direction simultaneously at a same degree of twist while the fluid flows through the first hose and the second hose.

17. The method according to claim 16, wherein flowing the fluid through the first hose and through the second hose is performed at substantially the same pressure prior to the twisting of the first hose and the second hose.

18. The method according to claim 16, wherein the device includes a first flow meter downstream from the first outlet through which the fluid flows and a second flow meter downstream from the second outlet through which the fluid flows, and further including the steps of measuring the flow rate of the fluid through the first flow meter and the second flow meter.

19. The method according to claim 16, wherein the device includes an encoder, and further including the step of measuring a degree of twist of the first inlet with the encoder.

20. The method according to claim 16, further including the step of visually analyzing the twist of first hose and the twist of second hose while they are twisted as the fluid flows therethrough.

* * * * *